United States Patent [19]
Spaulding

[11] Patent Number: 6,113,613
[45] Date of Patent: Sep. 5, 2000

[54] INTRAVASCULAR CATHETER HAVING A CAGE MEMBER SPANNING THE HOUSING WINDOW

[75] Inventor: Ronald Nicholas Spaulding, San Jose, Calif.

[73] Assignee: Guidant Corporation, Santa Clara, Calif.

[21] Appl. No.: 08/911,084

[22] Filed: Aug. 14, 1997

[51] Int. Cl.[7] .................................................. A61B 17/22
[52] U.S. Cl. ........................................................... 606/159
[58] Field of Search .................................... 606/159, 170, 606/171, 180; 604/22, 104

[56] References Cited

U.S. PATENT DOCUMENTS

| | | | |
|---|---|---|---|
| 3,614,953 | 10/1971 | Moss | 606/159 |
| 4,631,052 | 12/1986 | Kensey | 604/22 |
| 4,669,469 | 6/1987 | Gifford, III et al. | 606/159 |
| 4,867,157 | 9/1989 | McGurk-Burleson et al. | 606/170 |
| 4,921,484 | 5/1990 | Hillstead | 604/104 |
| 4,979,951 | 12/1990 | Simpson | 606/159 |
| 5,071,425 | 12/1991 | Gifford, III et al. | 606/159 |
| 5,074,841 | 12/1991 | Ademovic et al. | 604/22 |

*Primary Examiner*—Michael Buiz
*Assistant Examiner*—Vy Q. Bui
*Attorney, Agent, or Firm*—Blakely, Sokoloff, Taylor & Zafman LLP

[57] ABSTRACT

A catheter device for use in a biological conduit includes a catheter body having a proximal end and a distal end, a housing connected to the distal end of the catheter body, the housing including a window for invaginating biological tissue and a work element movably attached to operate within the housing, the window exposing the work element. A cage member is attached to the housing and partially covers the window, the cage member permitting a selective invagination of biological tissue therethrough into the window. When the catheter device is inserted in the biological conduit, the cage member selectively controls an invagination of tissue within the catheter device while preventing invagination of any stent material or invagination of walls of the biological conduit.

30 Claims, 3 Drawing Sheets

INTRAVASCULAR CATHETER HAVING A CAGE MEMBER SPANNING THE HOUSING WINDOW

BACKGROUND OF THE INVENTION

1. Field of the Invention

This invention relates generally to medical devices and especially to intravascular catheters designed to operate with respect to occlusions within a blood vessel. More particularly, this invention relates to catheters for debulking coronary artery lesions and for safely cleaning stents, which are wire frameworks that are compressed, delivered a balloon catheter and positioned across a segment of an artery.

2. Description of the Related Art

Medical science has long sought effective treatments for disease conditions involving stenosis (narrowing or obstruction) of the lumen (interior passage of the artery) of an artery. This condition, known generally as an occlusion, is found in patients suffering from atherosclerosis (accumulation of fibrous, fatty or calcified tissue in the arteries). An occlusion can manifest itself in hypertension (high blood pressure), ischemia (deficiency of circulation), angina (chest pain), myocardial infarction (heart attack), stroke, or death. An occlusion may be partial or total, may be soft and pliable or hard and calcified, and may be found at a great variety of sites in the arterial system including the aorta, the coronary and carotid arteries, and peripheral arteries.

Of particular interest to cardiac medicine are the often disabling or fatal occlusions occurring in the coronary arteries (arteries supplying the heart). Traditionally, coronary artery occlusions have been treated by performing coronary bypass surgery, in which a segment of the patient's saphenous vein is taken from the patient's leg and is grafted onto the affected artery at points proximal (upstream) and distal (downstream) to the occluded segment. The bypass often provides dramatic relief. However, it entails dangerous open chest surgery and a long, painful, costly convalescence in the hospital. Moreover, with the passage of time, the bypass patient's saphenous vein graft can also become occluded. If the patient has another saphenous vein, a second bypass procedure may be performed, once again entailing open chest surgery and prolonged hospitalization. Thereafter, if the underlying atherosclerotic disease process is not controlled, the prognosis is dismal.

Newer, minimally invasive procedures are now preferred in the treatment of arterial occlusions. These procedures use a catheter, a long, thin, highly flexible device which is introduced into a major artery through a small arterial puncture made in the groin, upper arm, or neck and is advanced and steered into the site of the stenosis. At the distal end of the catheter, a great variety of miniature devices has been developed for operating upon the stenosed artery.

The more popular minimally invasive procedures include percutaneous transluminal coronary angioplasty (PTCA), directional coronary atherectomy (DCA), and stenting. PTCA employs a balloon to mechanically dilate the stenosis. In PTCA, a steerable guidewire is introduced and advanced under fluoroscopic observation into the stenosed artery and past the stenosis. Next, a balloon-tipped catheter is advanced over the guidewire until it is positioned across the stenosed segment. The balloon is then inflated, separating or fracturing the atheroma (stenosed tissue). The hoped-for outcome is that, over time, the lumen will stay open.

In directional coronary atherectomy a catheter, containing a cutter housed in its distal end, is advanced over the guidewire into the stenosed segment. The housing is urged against the atheroma by the inflation of a balloon, so that part of the atheroma intrudes through a window in the side of the housing. Under fluoroscopic observation, the cutter is used to shave away the atheroma. The shavings are collected in the nosecone of the housing and withdrawn along with the catheter or flushed out of a flushing lumen running the length of the device.

Some examples of existing devices include U.S. Pat. No. 5,074,841 to Ademovic et al.; U.S. Pat. No. 4,669,469 to Gifford III et al.; and the curretting tool described in U.S. Pat. No. 4,867,157 to McGurk-Burleson et al. The devices described in these references, however, are solely optimized toward uses involving helical cutting blades, the cutting and grinding of flap-like pieces of atheromas, or a penetration into the patient's body of only a few centimeters. None of the devices disclosed in these patents, however, is effective in stented portions of the patient's vessels.

Stenting is a procedure in which a wire framework, known as a stent, is compressed and delivered a balloon catheter. The stent is positioned across the stenosed segment of the artery. The balloon is inflated, dilating the stent and forcing the stent against the artery wall. The hoped-for outcome is that the stent will hold the arterial lumen open for a prolonged period. Frequently, a stent is placed in an artery immediately following PTCA or DCA.

However, over time, the stent itself may become stenosed, as fatty or calcified tissue accumulates in and around the wire mesh or struts of the stent. This can happen for several reasons. One reason for this accumulation may be intimal hyperplasia which leads to tissue ingrowth within the wire mesh of the stent, resulting in in-stent re-stenosis. Another reason for the re-stenosis of the stented area may be a compliance mismatch between stented and non-stented areas. The type of and materials used for the stent may also lead to an auto-immunological response wherein the patient's body recognizes the stent as a foreign body and attempts to reject it. Antibodies may then cling to the wire mesh of the stent to such a degree as to eventually occlude the vessel and constrict blood flow. Still another reason may be that the patient has maintained the same lifestyle and eating habits as before the stenting procedure. Therefore, the same factors that lead to the original occlusion persist, and the arteries suffer from the same fatty deposits and plaque that created the first stenosis.

In these cases, and for whatever the underlying reason, fatty tissue and plaque grow in the interstitial spaces in the wire mesh of the stent, and eventually grow outside the stent to occlude the very vessel the stent was designed to maintain open. It is estimated that this in-stent re-stenosis occurs, for single stents in a discrete focal region, in approximately 12 to 20 percent of stenting cases. The re-stenosis rates for diffusely diseased vessels, which often require more than one stent, have been reported as high as 80 percent.

Currently, there is no effective method of treating in-stent re-stenosis. For example, one proposed solution involves the application of another stent to the occluded area of the first stent. In effect, this amounts to re-stenting the first stent. This procedure, however, is not an optimal solution, as the blood vessel may not support two stents, and re-stenting does not address the underlying problem of accumulated plaque or other fibrous material lodged within the stent wire mesh.

Another proposed solution to the problem of in-stent re-stenosis involves the use of balloon angioplasty. However, such a method may not be indicated in some applications, due to high re-stenosis rates. Indeed, balloon angioplasty has been reported to be ineffective due to the soft nature of some lesions, which mainly consist of smooth muscle cells migrating to form intimal hyperplasia. Balloon dilation also causes the tissue to extrude out into non-dilated areas, narrowing the lumen diameter and causing turbulent flow in such sites. Such turbulent flow is thought to be a contributing factor in the development of vascular occlusions. In addition, further dilation may cause further expansion of the stent, thereby causing more vessel injury due to stent strut/vessel interaction, which interaction may have contributed to the re-stenosis in the first place. Indeed, PTCA for in-stent re-stenosis has shown re-stenosis rates as high as 55 percent, even when the Mean Lumen Diameter (MLD) after dilation is within 3 to 5 percent of the original values.

The use of lasers, such as ELCA, has also been proposed, but lasers are expensive and limited in the amount of debulking that can be achieved.

What is desired, therefore, is a device for cleaning stents that have become occluded, to thereby remove the unwanted material and restore the full intended therapeutic effects of the arterial stent.

However, using a conventional atherectomy catheter to clean a stenosed arterial stent may not be the most effective therapy, as portions of the wire mesh of the stent may become invaginated along with the stenosed tissue. This undesirable invagination of the stent material can cause entanglement or cutting of the mesh in the atherectomy catheter cutter, or even the collapse of the stent. Even if the stent does not collapse, the wire mesh can become wound about the cutter element. To retract the catheter, thereafter, it is necessary to remove it, together with the entangled stent, from the patient's body, with potentially undesirable outcomes. Other undesirable outcomes of cutting a portion of the stent may occur if the inadvertently cut portion of the stent is not collected by the catheter and, instead, travels back to the cardiac muscle.

What is desired, therefore, is a device for the controlled invagination of the occluding material at the stent location without, however, running the risk of invaginating a portion of the wire mesh of the stent along with the stenosed tissue.

It is not only the stent material that can become undesirably invaginated in the cutter opening of the catheter. In some cases, the vessel walls can also be invaginated and cut by the cutter. In those cases, the vessel can be damaged, necessitating complex and more invasive repair work on the part of the physician, with accompanied increased risk for the patient. There has been a long felt need, by physicians and patients alike, for an atherectomy catheter which minimizes the probability of undue vessel damage during the DCA procedure proper.

What is desired, therefore, is an atherectomy catheter which will allow the physician to perform optimal atherectomy, that is, atherectomy which prevents the vessel walls from being damaged or cut by the working element during the DCA procedure. Specifically, what is desired is an atherectomy catheter which allows the undesirable stenotic material to become invaginated into the cutter or working element opening, but prevents the walls of the vessel from being so invaginated, cut or damaged by the cutter.

Moreover, in conventional atherectomy catheters equipped with a reciprocating or rotary cutter or abrasive working head or element, it is conceivable that the cutter or working element may break away from the cutter torque cable. Also, ejection of the cutting element from the catheter housing could occur because of, for example, a microfracture in the cutter, especially when such microfractures undergo the high magnitude stresses imposed by the extremely high rotational speeds of modern atherectomy catheter cutters, which speeds are on the order of 10,000 rpm.

What is desired, therefore, is a device for preventing damage to the vessel walls when the working element, such as a cutter or an abrasive element of an atherectomy catheter, accidentally becomes dislodged from the catheter housing.

In addition, in conventional catheters, there can occur a twisting or torquing of the housing during use, due to the high rotational speeds of the working element and the reciprocal motion imposed thereupon. The twisting of the housing then generates a corresponding twisting of the housing opening within the lumen. This occurs despite the presence of the balloon which is designed to keep the catheter housing stationary during use. Such twisting is undesirable, as the orientation of the housing opening determines the location of the cuts or abrasions carried out by the working element.

What is desired, therefore, is an atherectomy catheter which has greater structural resistance to forces which tend to twist the catheter housing during use.

Debulking a particular site of a coronary artery is a useful procedure often performed before the placement of a stent. This procedure provides a larger cross sectional area within which the stent can be implanted. Debulking also removes most of the lesion which would otherwise extrude to outside the stent/balloon boundaries. Debulking is also a very useful procedure in the case of eccentric lesions. In eccentric lesions, stents are more apt to expand into the healthier, more elastic side of the lumen, thereby causing injury to the healthier side of the artery. However, conventional debulking atherectomy catheters may damage the arterial walls, as a portion of the vessel walls become invaginated into the housing opening.

What is desired, therefore, is an atherectomy catheter which can be used for debulking arterial lesions but which, nevertheless, provides optimal protection against an undesired invagination of vessel wall into the housing opening.

SUMMARY OF THE INVENTION

It is, therefore, an object of the present invention to provide a device for cleaning stents that have become occluded.

It is an additional object of the present invention to provide a device for the invagination of stenotic tissue occluding an artery or other biological conduit at the stent location, the invagination being controlled so as to avoid invaginating a portion of the wire mesh or struts of the stent along with the stenosed tissue.

It is an additional object of the present invention to provide an atherectomy catheter which allows the cleaning of stenotic material from an arterial stent, while preventing the invagination of stent material, or accidental invagination of the vessel walls.

It is an additional object of the present invention to provide an atherectomy catheter which prevents the vessel walls from being damaged or cut by the working element of an atherectomy catheter.

It is an advantage of this invention to provide a device for preventing damage to the vessel walls when a working element, such as a cutter or an abrasive element of an atherectomy catheter, becomes disconnected from the catheter's cutter torque cable.

It is an additional advantage of the present invention to provide an atherectomy catheter which has increased structural resistance to forces which tend to twist the catheter housing during use.

It is an additional advantage of the present invention to provide an atherectomy catheter which can be advantageously used for debulking arterial lesions but which, nevertheless, provides optimal protection against an unwanted invagination of vessel walls into the housing window.

In accordance with the above objects and those that will be mentioned and will become apparent below, the catheter device for use in a biological conduit according to the present invention comprises:

a catheter body having a proximal end and a distal end;
 a housing connected to the distal end of the catheter body, the housing including a window for invaginating biological tissue;
 a work element movably attached to operate within the housing, the window exposing the work element; and
 a cage member attached to the housing and partially covering the window, the cage member permitting a selective invagination of biological tissue therethrough into the window.

It is an advantage of the present invention that, when the catheter device is inserted in the biological conduit, the cage member selectively controls an invagination of tissue within the catheter device while preventing invagination of stent material or invagination of walls of the biological conduit.

According to an exemplary embodiment, the cage member comprises a mesh of interwoven strands of material. According to another exemplary embodiment, the cage member comprises a plurality of thin parallel members, which may be disposed perpendicularly or in parallel to the longitudinal axis of the housing.

According to an additional embodiment, the cage member comprises a thin resilient screen having a plurality of openings therein for allowing passage of biological tissue into the housing while preventing invagination of vessel walls or stent material. The openings may be rectangular, circular, hexagonal, or most any suitable shape. The cage member may comprise an arcuate outer surface which substantially matches an arcuate outer surface of the housing of the catheter device.

According to an embodiment of the present invention, the cage member is made of the same material as the housing of the catheter device. Alternatively, the cage member may be made of a different material as is the housing. The cage member may be made from a material comprising one or more of the following: stainless steel, gold, carbide, hard plastic, platinum, titanium, and nickel. Alternatively still, the cage member may be formed of a shape memory material, whereby the cage member returns to an original shape after undergoing a deformation.

According to another exemplary embodiment of the present invention, a stent cleaner catheter device for cleaning a stent inserted within a biological conduit comprises:

a catheter body having a proximal end and a distal end;
 a housing connected to the distal end of the catheter body, the housing including a window and a thin screen of resilient material spanning the window for selectively invaginating biological tissue at a stent location, while preventing invagination of walls of the biological conduit and stent material; and
 a work element movably attached to operate within the housing, the window exposing the work element through the thin screen.

An advantage of this embodiment is that, when the stent cleaner catheter device is inserted in the biological conduit, the thin screen and the work element cooperate to clean the stent by selectively invaginating, at the stent location, the biological tissue through the thin screen, the thin screen preventing damage to the stent and to the biological conduit walls by the work element as the biological tissue is removed from the stent location.

Another advantageous embodiment of the device according to the present invention comprises:

a catheter body having a proximal end and a distal end;
 a housing connected to the distal end of the catheter body, the housing including a window for invaginating biological tissue, the housing including an integral cage spanning the window, the integral cage being formed of a plurality of cage member elements defining a plurality of interstitial spaces therebetween, the interstitial spaces being dimensioned so as to prevent invagination of stent material therethrough; and
 a work element movably attached to operate within the housing, the window exposing the work element through the integral cage.

An advantage of this embodiment is that, when the catheter device is inserted in the biological conduit, the integral cage partially shields the work element to selectively control an invagination of tissue within the catheter device through the interstitial spaces while preventing invagination of stent material.

BRIEF DESCRIPTION OF THE DRAWING

For a further understanding of the objects and advantages of the present invention, reference should be had to the following detailed description, taken in conjunction with the accompanying drawings, in which like parts are given like reference numerals and wherein.

DETAILED DESCRIPTION OF THE INVENTION

Figure 1:
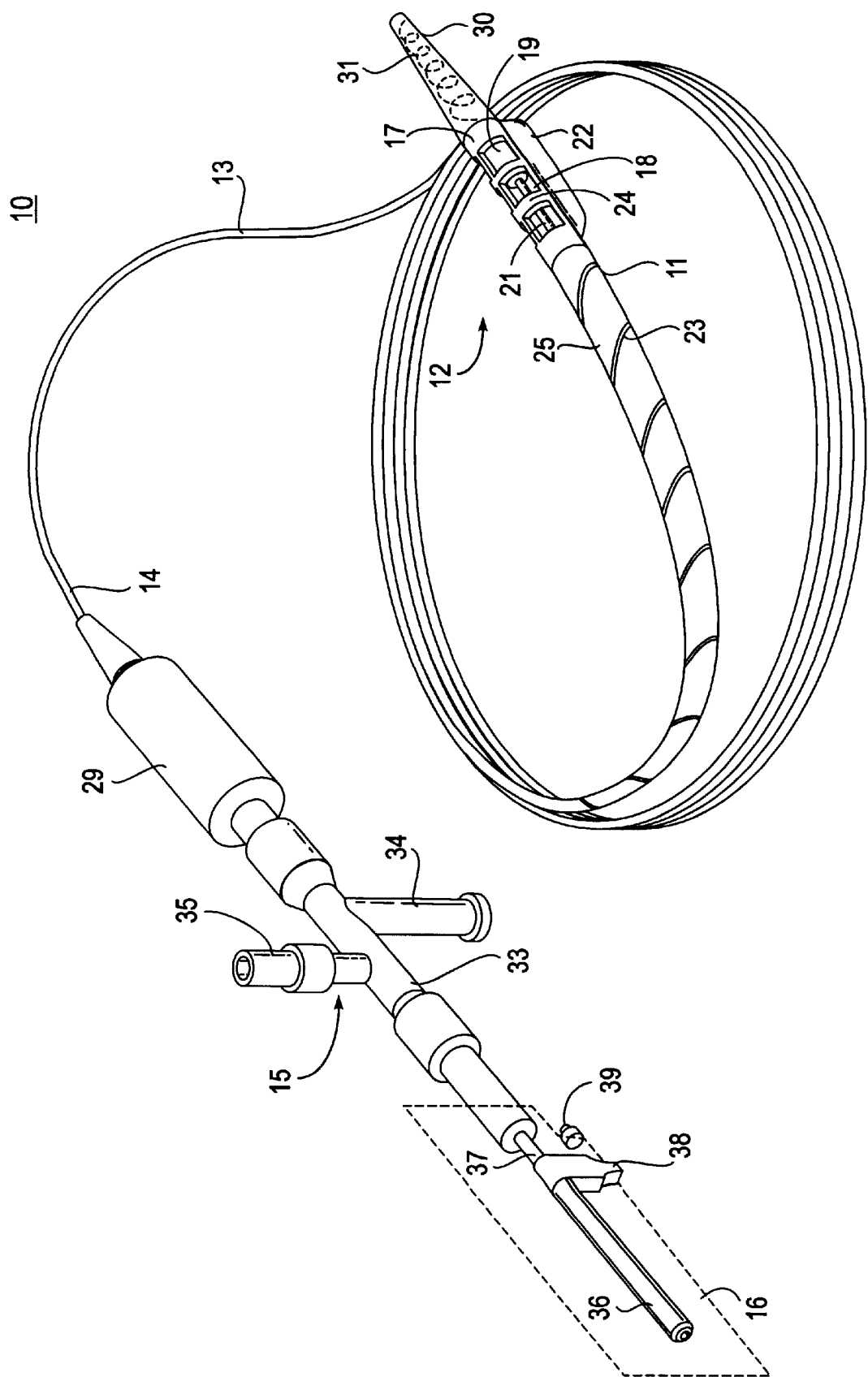
FIG. 1 shows an embodiment of an atherectomy catheter according to the present invention.

FIGS. 1–6 schematically depict an atherectomy catheter 10 embodying features of the invention. The invention will now be described with respect to FIG. 1, which illustrates an atherectomy catheter according to the invention. The catheter 10 includes a distal portion 11 having a cutter head assembly 12, an elongated catheter shaft 13 and a proximal portion 14 having a triple arm manifold assembly 15, and drive assembly 16, shown only in phantom lines.

The cutter head assembly 12 includes a cylindrical housing 17, a window 18 and a work element, such as a cutter blade 19, which work element is slidably disposed within an inner chamber of the housing 17 for both reciprocal and rotational movement. The movement of the cutter blade 19 is effected by the cutter torque cable 21 which is secured to the proximal end of the cutter blade 19.

Inflatable positioning balloon 22 is secured to the exterior of the housing 17 on a side opposite the window 18 so that, upon its inflation within the stenotic region of the patient's artery, the housing will be pressed against the stenotic material to cause some of it to be invaginated through the cage member 24 into the window 18, where the cutter blade 19 can sever it from the remaining stenotic material on the stent or arterial wall. An inflation lumen 23 is disposed within the outer tubular member 25 of the catheter shaft 13, to direct inflation fluid to the interior of the balloon 22. The cutter torque cable 21 is attached to the rotator 29. The proximal end of the rotator 29 is rotatably secured to the manifold assembly 15 so that the cutter torque cable can be rotated by rotation of the rotator 29 without moving the manifold assembly 15.

A flexible nosecone 30 is secured to the distal end of the housing 17 to prevent traumatic engagement with the artery wall when the catheter 10 is advanced through the patient's arteries. An inner coil or spring 31 is disposed within the nosecone 30 to provide the nosecone 30 with a degree of resiliency.

The triple arm manifold assembly 15 on the proximal portion 14 of the catheter 10 generally includes a manifold body 33 and an inflation arm 34 and a flush arm 35. The inflation arm 34 is in fluid communication with the inner lumen of the inflation tube 23 for delivery of inflation fluid to the interior of the balloon 22. The flush arm 35 is in fluid communication with the interior of the housing 17 and is adapted to the direct irrigation of radioopaque liquid to the interior of the housing 17.

The drive assembly 16 is interconnected to the cutter torque cable 21 by means of a connector 36. The connector 36 is, in turn, connected to an intermediate drive shaft 37. A finger actuated lever 38 is rotatably mounted onto the intermediate drive shaft 37 but is fixed thereto to prevent longitudinal movement relative to the intermediate drive shaft 37, so that longitudinal movement of the finger actuated lever 38 will cause longitudinal movement of the cutter blade 19 within the housing 17. The operation of the drive assembly 16 is initiated by the actuation of the switch 39 which causes the rotation of the cutter torque cable 21 and the cutter blade 19 secured thereto.

Figure 2:
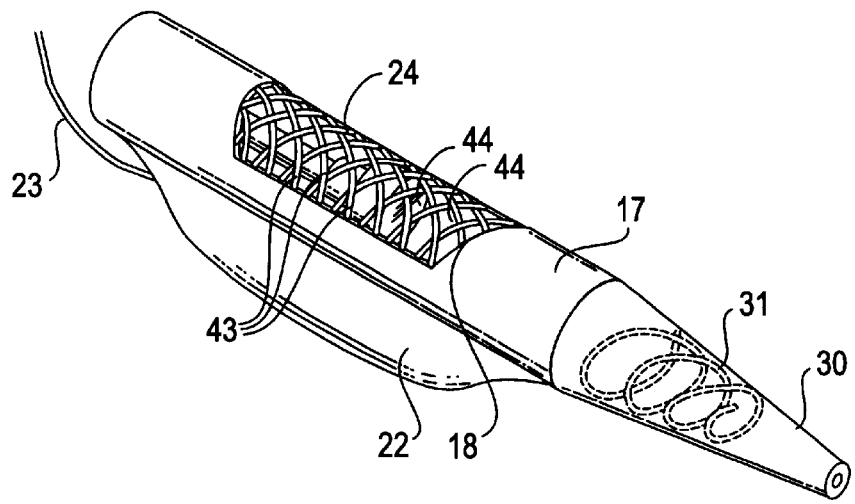
FIG. 2 shows an embodiment of the distal section of the atherectomy catheter according to the present invention.

FIG. 2 shows a preferred embodiment of the invention. The atherectomy catheter cutter head assembly 12 includes a housing 17, which has a window 18. The window 18 exposes the working element of the atherectomy catheter. In FIGS. 1 through 6, a cutter blade 19 is shown as the working element. However, the present invention is not to be limited thereto. For example, the working element may also be an abrasive element, such as a diamond burr.

The window 18 is spanned by a cage member 24. The cage member 24 includes a plurality of cage member elements 43 which define a plurality of interstitial spaces 44 therebetween, as shown in FIG. 2. The interstitial spaces 44 allow the invagination of occluding biological tissue, but prevent vessel walls or stent mesh or struts from invaginating into the window of the housing 17. The cage member 24, as shown in FIG. 2, may be a wire mesh of interwoven and braided strands. The cage member 24 may be of the same material as the housing 17, such as stainless steel. Alternatively, the cage member 24 may be made of a different material than the housing 17. The cage member 24 may be made from stainless steel, gold plated stainless steel, from titanium, platinum, or from an alloy of the aforementioned materials or from an alloy containing, for example, nickel. Alternatively, the cage member 24 may be made of hard plastic, carbide, or the like.

The cage member 24, in operation, prevents the invagination of any stent struts by preventing the stent from coming into contact with the cutter 19. Therefore, the catheter according to the present invention is ideally suited to stent cleaning, in which the catheter can be positioned adjacent a re-stenosed stent, the balloon 22 inflated, and the cutter put into operation. By virtue of the cage member 24, only the tissue occluding the stent will be invaginated into the window 18 through the cage member 24, and the wire mesh and struts of the stent will be prevented from coming into contact with or cut by the cutter 19. In this manner, the unwanted material can be removed from the stent site, and the full intended therapeutic effects of the arterial stent can be restored.

The cage member 24, because of the constraint it imposes on the top of the housing window 18, keeps the vessel wall from being invaginated into the housing window 18. The cage member 24 also provides protection against possible disconnection of the work element, or cutter blade 19, from its cutter torque cable 21. Indeed, the catheter according to the present invention constrains the work element 19, so as to prevent it from damaging or perforating the vessel wall should it, for any reason, become disconnected from the cutter torque cable 21, or possibly ejected from the housing 17. This is a significant safety advantage, as the work element 19 typically rotates at a high rate of speed, and has the potential to inflict some measure of damage to the arterial wall should it come loose.

The cage member 24 also imparts additional structural rigidity to the housing 17, as compared to an identical housing without such a cage member. This is advantageous in performing DCA or stent cleaning operations, in which a twisting of the housing 17 could damage the catheter and possibly injure the patient.

An atherectomy catheter equipped with such a cage member 24 also provides the physician with a debulking tool that can be used without concern over possible damage to the vessel wall. Indeed, the cage member 24 constrains the cutter 19 and does not allow the vessel walls to invaginate therethrough into the window 18. Therefore, the physician is able to aggressively debulk the lesion site, either prior to emplacement of a stent, or in arterial locations where stents are not therapeutically effective, without concern of accidental invagination the vessel wall through the cage member 24 into the window 18.

FIGS. 3–6 are identical to FIG. 2, but for the structure of the cage member. In FIGS. 3–6, therefore, like reference numbers denote like elements, and the description thereof will be omitted.

Figure 3:
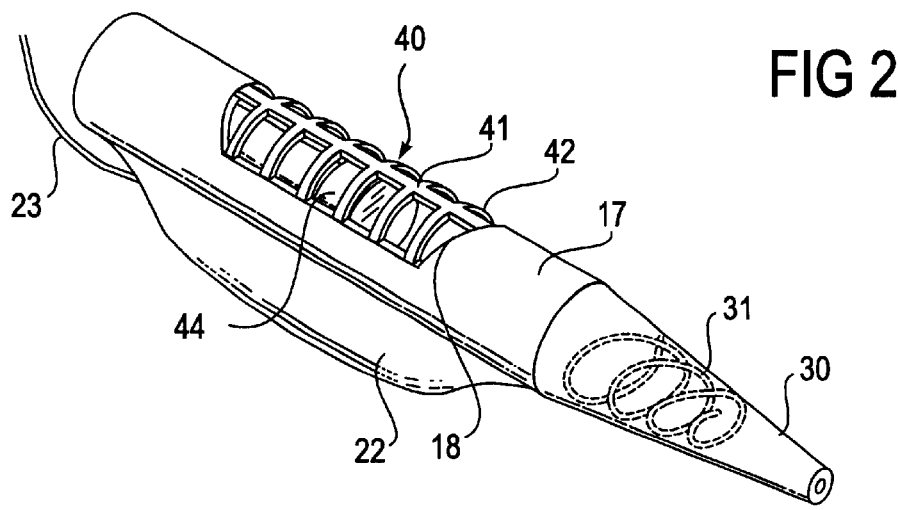
FIG. 3 shows another embodiment of the distal section of an atherectomy catheter according to the present invention.

In FIG. 3, the cage member is referenced generally by numeral 40. Cage member 40 is formed of a thin longitudinal member 41 spanning the middle of window 18 from its distal to its proximal end. Attached to the thin longitudinal member 41 are a plurality of thin parallel members 42, the thin parallel members 42 being disposed perpendicularly to the longitudinal member 41 and spanning the space between the longitudinal member 41 and the edge of the window 18, on either side of the longitudinal member 41. The cage member of FIG. 2, as well the cage members illustrated in FIGS. 1 and 3–6, comprise an arcuate outer surface which substantially matches the arcuate outer surface of the housing 17. The plurality of thin parallel members are spaced substantially equidistant from one another at a distance which forms interstitial spaces 44 of a size and shape which prevents invagination of stent material, but allows the invagination of occlusive material. The number of longitudinal and parallel members, as well as their mutual spacing and orientation, can be varied according to the application envisaged, to gain the optimum therapeutic effect, as the person of skill in this art will immediately realize.

Figure 4:
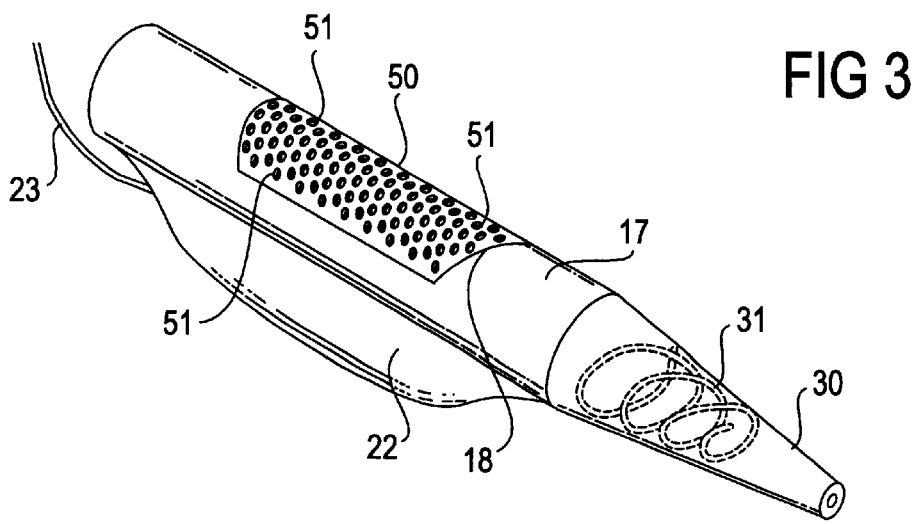
FIG. 4 shows another embodiment of the distal section of the atherectomy catheter according to the present invention.

Another embodiment of the present invention is shown in FIG. 4. In FIG. 4, the cage member is a thin resilient screen 50 having a plurality of openings 51 therein. The openings may have most any shape, including circular, elliptical, square, rectangular, triangular, and the like. The stenosed tissue is invaginated through the openings in the thin screen 50. The size of the openings 51 will be dictated by the application, as well as by the speed at which it is desired to remove the occlusive material. Harder deposits within a patient's arteries may require larger openings 51, while softer, fatty deposits may be effectively removed using openings 51 of smaller size. The arcuate outer surface of the thin resilient screen 50 substantially matches the arcuate outer surface of the housing 17.

Figure 5:
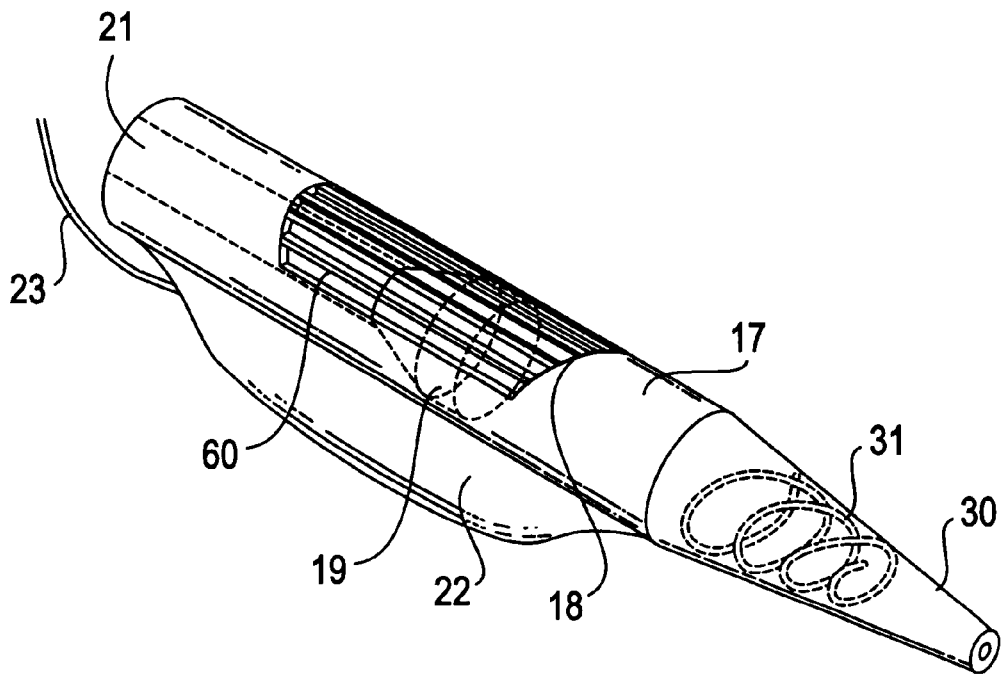
FIG. 5 shows another embodiment of the distal section of the atherectomy catheter according to the present invention.

FIG. 5 shows yet another embodiment of the atherectomy catheter according to the present invention. In FIG. 5, the cage member is constituted by a plurality of thin members 60 disposed parallel to the longitudinal axis of the catheter housing 17. The number of thin members 60 and their mutual spacing may vary according to the application. To best illustrate the emplacement of the cutter 19 within the housing 17, the cutter 19 and the cutter torque cable, in FIG. 5, are shown in phantom lines. Alternatively, the thin members 60 may be disposed perpendicularly to the longitudinal axis of the catheter 10, or at another angle relative thereto.

The cage member 24, 40, 50 or 60 may be of the same material as the housing 17, such as stainless steel. Alternatively, the cage member 24, 40, 50 or 60 may be made of a different material than the housing 17. For example, the cage member 24, 40, 50 or 60 may be made from stainless steel, gold plated stainless steel, titanium, platinum, an alloy of the aforementioned metals, or from an alloy containing, for example, nickel. Alternatively, the cage member 24, 40, 50 or 60 may be made of carbide, hard plastic or other synthetic material. Alternatively still, the cage member 24, 40, 50 or 60 may be made of a shape memory material. This allows the cage member to regain its original shape after undergoing deformation by, for example, hard or calcified deposits within the arterial lumen.

The cage member 24, 40, 50 or 60 in operation, prevents the invagination of stent struts by preventing the stent from coming into contact with the cutter 19. Therefore, the catheter shown in FIG. 1 and its alternative embodiments shown in FIGS. 2–6, are ideally suited to stent cleaning, in which the catheter can be positioned adjacent a re-stenosed stent, the balloon 22 inflated, and the cutter 19 put into operation. By virtue of the presence of the cage member 24, 40, 50 or 60, only the tissue occluding the stent will be invaginated into the window 18 through the cage member 24, 40, 50 or 60 and the wire mesh and struts of the stent will be prevented from coming into contact with the cutter 19. In this manner, the unwanted material can be removed from the stent site, and the full intended therapeutic effects of the arterial stent can be restored.

The cage member 24, 40, 50 or 60, by virtue of the constraint it imposes on the top portion of the housing window 18, keeps the vessel wall from invaginating into the housing window 18.

Figure 6:
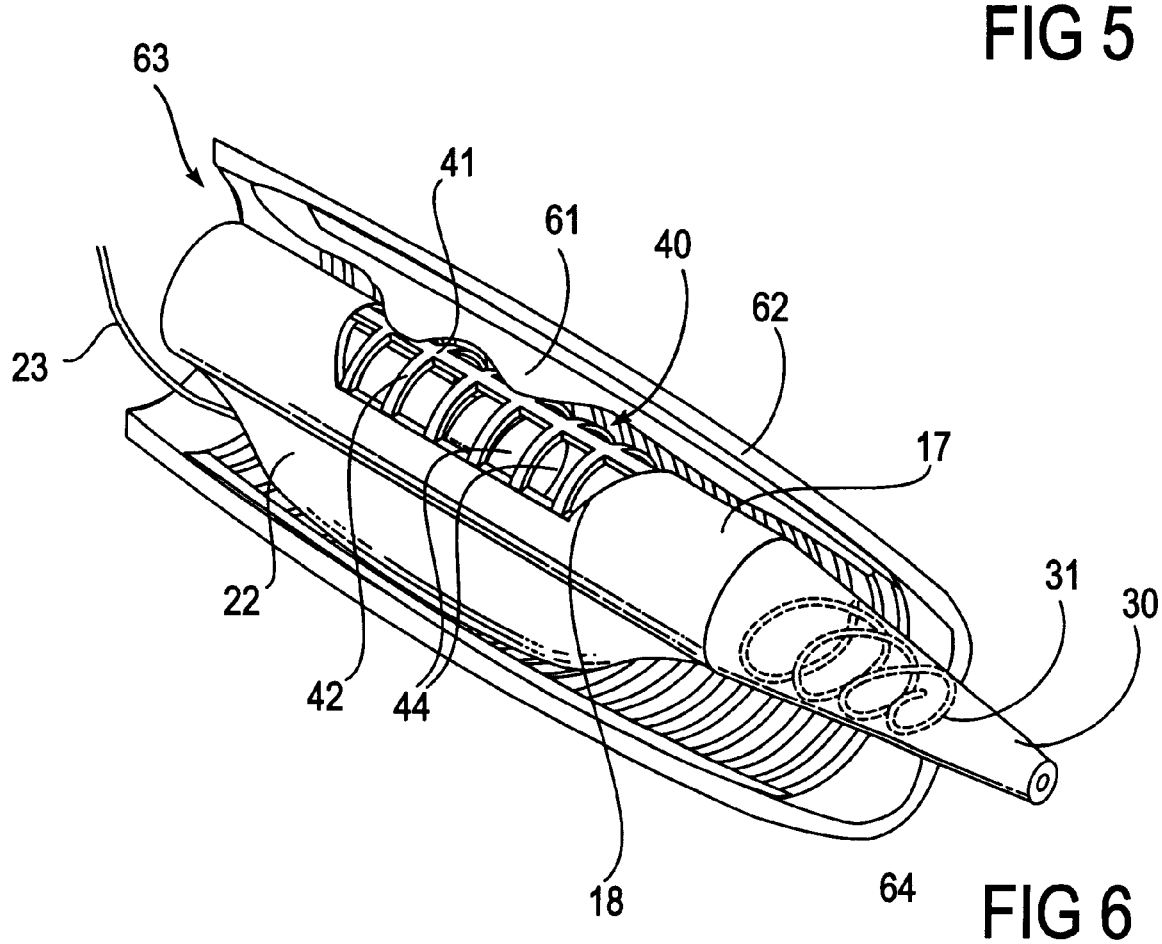
FIG. 6 shows the distal section of the atherectomy catheter according to the present invention, inserted into a stented biological conduit, during use.

This is shown in FIG. 6, which illustrates an atherectomy catheter according to the present invention in use, inserted into a patient's stented artery 63. As shown in FIG. 6, the cage member 40 selectively allows the invagination of stenosed material 61 while preventing the invagination of the struts of stent 64. This is because the thin longitudinal and parallel members of the cage member 40 are spaced so as to create interstitial spaces 44 of a size and shape which prevents invagination of the vessel walls or struts of the stent 64, but allow the invagination of the stenosed material 61.

The cage member 24, 40, 50 and 60 also provides protection against accidental disconnection of the cutter 19 from the cutter torque cable 21. Indeed, the catheter, according to the present invention, constrains the cutter blade 19, so as to prevent it from causing damage to the vessel wall should it, for any reason, become disconnected from the cutter torque cable 19, or somehow ejected from the housing 17. This is a significant safety advantage, as the cutter blade 19 typically rotates at a high rate of speed.

The cage members 24, 40, 50 or 60 also impart additional structural rigidity to the housing 17, compared to an identical housing without such a cage member. This is advantageous in performing DCA or stent cleaning operations, in which a twisting of the housing 17 could damage the catheter and possibly injure the patient.

The cage member 24, 40, 50 and 60 of the housing 17 also provide the physician with a highly effective debulking tool that can be used without concern of damaging the vessel wall. Indeed, the cage members 24, 40, 50 and 60 constrain the cutter blade 19 and do not allow the vessel walls to invaginate into the window 18. Therefore, the physician can aggressively debulk the lesion site, either prior to emplacement of a stent or, in cases where stents are not therapeutically effective, without concern of invaginating the vessel wall into the window 18, due to the presence of the cage member 24, 40, 50 or 60.

While the foregoing detailed description has described several embodiments of this invention, it is to be understood that the above description is illustrative only and not limiting of the disclosed invention. For example, the cage member can assume most any configuration which achieves the goals of preventing the unwanted invagination of stent material and vessel walls, increasing the structural rigidity of the housing, constraining the cutter blade or work element in the event of malfunction or failure of the cutter torque cable or the work element itself, providing an effective debulking tool, and the other goals and advantages specifically enumerated or apparent from the description above. For example, the spacing between and the orientation of the cage member elements can be varied at will, depending upon the application at hand. Thus, the invention is to be limited only by the claims as set forth below.

What is claimed is:

1. A catheter device for use in a biological conduit, comprising:

a catheter body having a proximal end and a distal end;

a housing connected to the distal end of the catheter body, the housing including a window for invaginating biological tissue;

a work element movably attached to operate within the housing, the window exposing the work element; and a cage member attached to the housing and partially covering the window, the cage member including a mesh of interwoven strands of material; and the cage member permitting a selective invagination of biological tissue therethrough into the window, such that when the catheter device is inserted in the biological conduit, the cage member selectively controls an invagination of tissue within the catheter device while preventing invagination of stent material or invagination of walls of the biological conduit.

2. The catheter device of claim 1, wherein the cage member comprises a plurality of thin parallel members.

3. The catheter device of claim 2, wherein the plurality of thin parallel members is disposed perpendicularly to a longitudinal axis of the housing of the catheter device.

4. The catheter device of claim 2, wherein the plurality of thin parallel members is disposed parallel to a longitudinal axis of the housing of the catheter device.

5. The catheter device of claim 1, wherein the cage member comprises a thin resilient screen having a plurality of openings therein for allowing passage of biological tissue into the window while preventing invagination of vessel walls or stent material.

6. The catheter device of claim 5, wherein each of the plurality of openings has one of a rectangular, circular and hexagonal shape.

7. The catheter device of claim 1, wherein the cage member comprises an arcuate outer surface which substantially matches an arcuate outer surface of the housing.

8. The catheter device of claim 1, wherein the cage member is made of a same material as the housing of the catheter device.

9. The catheter device of claim 1, wherein the cage member is made of a different material as is the housing.

10. The catheter device of claim 1, wherein the cage member is made from a material comprising at least one of stainless steel, gold, carbide, hard plastic, platinum, titanium and nickel.

11. The catheter device as claimed in claim 1, wherein the cage member is made of a shape memory material, whereby the cage member returns to an original shape after undergoing a deformation.

12. A stent cleaner catheter device for cleaning a stent inserted within a biological conduit, comprising:
    a catheter body having a proximal end and a distal end;
    a housing connected to the distal end of the catheter body, the housing including a window and a thin screen of resilient mesh material spanning the window for selectively invaginating biological tissue at a stent location, while preventing invagination of walls of the biological conduit and stent material; and
    a work element movably attached to operate within the housing, the window exposing the work element through the thin screen,
    such that when the stent cleaner catheter device is inserted in the biological conduit at the stent location, the thin screen and the work element cooperate to clean the stent by selectively invaginating the biological tissue through the thin screen, the thin screen preventing damage to the stent and to the biological conduit walls by the work element as the biological tissue is removed from the stent location.

13. The catheter device of claim 12, wherein the thin screen includes a mesh of interwoven strands of material.

14. The catheter device of claim 12, wherein the thin screen includes a plurality of openings therein for allowing passage of biological tissue into the housing while preventing invagination of vessel walls or stent material.

15. The catheter device of claim 14, wherein each of the plurality of openings has one of a rectangular, circular and hexagonal shape.

16. The catheter device of claim 12, wherein the thin screen has an arcuate outer surface which substantially matches an arcuate outer surface of the housing.

17. The catheter device of claim 12, wherein the thin screen is made of a same material as the housing of the catheter device.

18. The catheter device of claim 12, wherein the thin screen is made of a different material than the housing.

19. The catheter device of claim 12, wherein the thin screen is made from a material comprising at least one of stainless steel, gold, carbide, hard plastic, platinum, titanium and nickel.

20. The catheter device as claimed in claim 12, wherein the thin screen is made of a shape memory material, whereby the cage member returns to an original shape after undergoing a deformation.

21. A catheter device which prevents invagination of stent material, for use in a biological conduit, comprising:
    a catheter body having a proximal end and a distal end;
    a housing connected to the distal end of the catheter body, the housing including a window for invaginating biological tissue, the housing including an integral cage spanning the window, the integral cage being formed of a plurality of interwoven cage member elements defining a plurality of interstitial spaces therebetween, the interstitial spaces being dimensioned so as to prevent invagination of stent material therethrough; and
    a work element movably attached to operate within the housing, the window exposing the work element through the integral cage,
    such that when the catheter device is inserted in the biological conduit, the integral cage partially shields the work element to selectively control an invagination of tissue within the catheter device through the interstitial spaces while preventing invagination of stent material.

22. The catheter device of claim 21, wherein the plurality of cage member elements are interwoven strands of material.

23. The catheter device of claim 21, wherein the plurality of cage member elements is disposed perpendicularly to a longitudinal axis of the housing of the catheter device.

24. The catheter device of claim 21, wherein the plurality of cage member elements is disposed parallel to a longitudinal axis of the housing of the catheter device.

25. The catheter device of claim 21, wherein each of the plurality of interstitial spaces has one of a rectangular, circular and hexagonal shape.

26. The catheter device of claim 21, wherein the integral cage comprises an arcuate outer surface which substantially matches an arcuate outer surface of the housing.

27. The catheter device of claim 21, wherein the integral cage is made of a same material as the housing of the catheter device.

28. The catheter device of claim 21, wherein the integral cage is made of a different material from the housing.

29. The catheter device of claim 21, wherein the integral cage is made from a material comprising at least one of stainless steel, gold, carbide, hard plastic, platinum, titanium, and nickel.

30. The catheter device as claimed in claim 21, wherein the integral cage is made of a shape memory material, whereby the integral cage returns to an original shape after undergoing a deformation.

* * * * *